United States Patent [19]

Altura et al.

[11] Patent Number: 6,100,095
[45] Date of Patent: Aug. 8, 2000

[54] IONIZED MAGNESIUM$^{2+}$ CONCENTRATIONS IN BIOLOGICAL SAMPLES

[75] Inventors: Bella T. Altura; Burton M. Altura, both of Beechhurst, N.Y.

[73] Assignee: The Research Foundation of the State University of New York

[21] Appl. No.: 08/398,814

[22] Filed: Mar. 6, 1995

Related U.S. Application Data

[63] Continuation of application No. 07/681,940, Apr. 8, 1991, abandoned.

[51] Int. Cl.$^7$ .................................................. G01N 33/20
[52] U.S. Cl. ............................................. 436/79; 204/403
[58] Field of Search ......................... 436/74, 79; 204/403

[56] References Cited

U.S. PATENT DOCUMENTS

| | | | |
|---|---|---|---|
| 4,448,770 | 5/1984 | Epting | 424/153 |
| 4,752,479 | 6/1988 | Briggs et al. | . |
| 4,954,349 | 9/1990 | Sheth et al. | 424/461 |
| 5,108,767 | 4/1992 | Mulchandani et al. | 426/72 |
| 5,350,518 | 9/1994 | Hiti et al. | 210/638 |

OTHER PUBLICATIONS

Danielson, B.G. et al. "The Determination of Ultrafiltrable Calcium and Magnesium in Serum". Ups J. Med. Sci. 87(1) p. 43–53, 1982.
Wybenga, D.R. et al. "Determination of Ionized Calcium in Serum that has been Exposed to Air". Clin. Chem. 22/7, p. 1009–1011, 1976.
Wortsman, J. et al. "A Rapid Method for the Determination of Ultra Filterable Calcium in Serum". J. Lab. Clin. Med. 98 (5) p. 691–696, 1981.
Maier, H. et al. "Investigation on the Performance of Calcium Selective Disc–Electrodes with Electrically Charged and Neutral Ligands in Anaerobic Serum Measurements". Res. Exp. Med. 172/1, p. 75–81, 1978.
Mauskop, Alexander; Altura, Bella T.; Cracco, Roger Q.; and Altura Burton M., "Serum Ionized Magnesium Levels in Patients with Tension–type Headaches". Tension–type Headache: Classification, Mechanisms, and Treatment, ed. by J. Olsen and J. Schoenen. Raven Press. Ltd., New York, pp. 137–140 (1993).
Altura, B.M. and Altura B.T., "Cardiovascular Risk Factors and Magnesium: Relationship to Atherosclerosis, Ischemic Heart Disease and Hypertension". Magnesium and Trace Elements, 1991–92; 10: 182–192.
Markell, M.S.; Altura, B.T.; Barbour, R.L.; and Altura, B.M. "Ionized and total magnesium levels in cyclosporin–treated renal transplant recipients: relationship with cholesterol and cyclosporin levels". Clinical Science (1993) 85, 315–318.
MacFate, R.P., "Introduction to the Clinical Laboratory", Year Book Medical Pub., Inc., Chicago, pp. 257–259 (1972).
Henry, J.G., "Chapter 9 Clincal Chemistry", In: Clinical Diagnosis by Laboratory Methods 15th Edition, I. Editors: Davidsohn and J.B. Henry, W.B. Saunders Co., Philadelphia, pp. 516–524 (1974).

Mauskop, A. et al., "Deficiency in Serum Ionized Magnesium but not Total Magnesium in Patients With Migraines. Possible Role of ICa$^{2+}$ Ration", Headache Journal, vol. 33 No. 3, pp. 135–138 (Mar. 1993).
Handwerker, S.M. et al., Ionized Magnesium and Calcium Levels in Umbilical Cord Serum of Pregant Women With Transient Hypertension During Labor, American Journal of Hypertension, vol. 6, pp. 542–545 (1993).
Altura, B.T. et al., "A new Method for the Rapid Determination of Ionized Mg$^{2+}$ in Whole Blood, Serum and Plasma", Meth. Find. Exp. Clin. Pharmacol., vol. 14 No. 4, pp. 297–304 (1992).
Altura, B.M. et al., "Magnesium Ions and Contraction of Vascular Smooth Muscles: Relationship to Some Vascular Disease", Federation Proceedings, vol. 40 No. 12, pp. 2672–2679 (Oct. 1981).
Altura, B.M. et al., "Magnesium Deficiency and Hypertension" Correlation Between Magnesium–Deficient Diets and Microcirculatory Changes in Situ, Science, vol. 223, pp. 1315–1317 (Mar. 23, 1984).
Walser, M., Ion Association. VI. Interactions Between Calcium, Magnesium, Inorganic Phosphate, Cirate and Protein in Normal Human Plasma. J. Clin. Investigation, vol. 40, pp. 723–730 (Jan.–Jun. 1961).
Resnick, L.M.; Gupta, R.K.; Laragh, J.H.; Alderman, M.H.; Altura, B.M., "Intracellular and extracellular magnesium depletion in Type 2 (non–insulin–dependent) diabetes mellitus". Diaetologia (1993) 36: 767–770.
Handwerker, Sara M., M.D.; Altura, Bella T., Ph.D.; Royo, Blas, M.D.; and Altura, Burton M., Ph.D., "Ionized Serum Magnesium Levels in Umbilical Cord Blood of Normal Pregnant Women at Delivery: Relationship to Calcium, Demographics, and Birthweight". American Journal of Perinatology, vol. 10, No. 5, pp. 392–397 (Sep. 1993).
Altura, Burton M.; Altura, Bella T.; and Gupta, Raj K., "Alcohol Intoxication Results in Rapid Loss in Free Magnesium in Brain and Disturbances in Brain Bioenergetics: Relation to Cerebrovasospasm, Alcohol–Induced Strokes, and Barbiturate Anesthesia–Induced Deaths". Magnesium and Trace Elements, 1991–1992; 10: 122–135.
Oesch, U., et al., "Ion–Selective Membrane Electrodes for Clinical Use", Clin. Chem., 32/8, 1448–1459 (1986).
Dinten, O. et al., "Lifetime of Neutral–Carrier–Based Liquid Membranes In Hqueous Samples and Blood and the Lipophilacity of Membrane Components", Anal. Chem. 63, pp. 596–603 (1991).

Primary Examiner—David A. Redding
Attorney, Agent, or Firm—Morgan & Finnegan, L.L.P.

[57] ABSTRACT

The present invention provides a method for preparing and storing biological samples prior to measuring ionized Mg$^{2+}$ concentrations in order to obtain accurate and reproducible readings. A novel method for accurately reading ionized magnesium ion concentrations in biological samples is provided. A method for monitoring ionized Mg$^{2+}$ concentrations and ionized Ca$^{2+}$:Mg$^{2+}$ ratios in a patient, useful in diagnosing and prognosing disease states including cardiopulmonary bypass surgery, hypertension, abnormal pregnancy, head trauma, cardiac diseases, lung diseases, pre-eclampsia, eclampsia, migraine, renal diseases, and fetal abnormalities is provided as well as a method of treating a patient with ionized Mg$^{2+}$.

22 Claims, 3 Drawing Sheets

IONIZED MAGNESIUM$^{2+}$ CONCENTRATIONS IN BIOLOGICAL SAMPLES

This is a file-wrapper-continuation of application Ser. No. 07/681,940, filed on Apr. 8, 1991 now abandoned.

This invention was made with government support from Grant Number 2RO1AA0867404 awarded by the National Institutes of Health. The government has certain rights in the invention.

BACKGROUND OF THE INVENTION

Magnesium (Mg) is the second most abundant cation in the body [Altura, B. M. et al., Drugs 28 (Suppl.I):120–142, 1984]. It is cofactor for more than 325 cellular enzyme involved in cellular energy production and storage, protein synthesis, DNA and RNA synthesis, cell growth and reproduction, adenylate cyclase synthesis, maintenance of cellular electrolyte composition, and stabilization of mitochondrial membranes [Altura, B. M. et al, Drugs 28 (Suppl.I):120–142, 1984; Wacker, W. E. C. *Magnesium and Man,* Harvard Univ. Press, Cambridge, 1980]. As a consequence of these biochemical activities, Mg plays a pivotal role in control of neuronal activity, cardiac excitability, neuromuscular transmission, muscular contraction, and vasomotor tone [Altura, B. M. et al., Drugs 28 (Suppl.I) :120–142, 1984; Wacker, W. E. C. *Magnesium and Man,* Harvard Univ. Press, Cambridge, 1980; Altura, B. M. et al., in: *Metal Ions in Biological Systems,* ed. by H. Sigel and A. Sigel, Vol 26:Compendium on Magnesium and Its Role in Biology, Nutrition, and Physiology, pp 359–416, Marcel Dekker, Inc. New York, 1990].

Most clinical data of Mg determinations are derived from blood levels of total Mg (Wacker, W. E. C. *Magnesium and Man,* 1980; Elin, R. J. Clin. Chem. 33:1965–1970, 1987). Total serum Mg concentrations reflect protein-bound (30–40%), chelated (7–12%), and free or ionized Mg (Mg$^{2+}$) (60–70%) fractions. The exact proportion of these fractions has been extremely difficult to determine precisely, and, moreover, there is no way to rapidly make such determinations. Precise information about Mg activity is pivotal to our understanding of Mg metabolism. The free or ionized form (Mg$^{2+}$) is the active form of the mineral (Wacker, W. E. C. *Magnesium and Man,* 1980; Elin, R. J. Clin. Chem. 33:1965– 1970, 1987; Ryan, M. F. Ann. Clin. Biochem. 28:19–26, 1991). Alterations in circulating protein levels (primarily albumin), which are seen in numerous pathophysiologic states, will alter the interpretation of Mg status (very similar to calcium) (Elin, R. J. Clin. Chem. 33:1965–1970, 1987).

Although numerous methods are available clinically, to determine total Mg in serum, plasma, urine, cerebral spinal fluid and other body fluids (e.g., atomic absorption spectrophotometry, atomic emission spectrophotometry, colorimetry, fluorometry, compleximetry and chromatograph for quantifying total Mg), none of these can determine ionized or free Mg$^{2+}$ (Elin, R. J. Clin. Chem. 33:1965–1970, 1987; Wills, M. R. et al. Magnesium 5:317–327, 1986).

Until the present invention, the only method for assessing free Mg$^{2+}$ in biological samples was an ultrafiltration procedure (Wacker, W. E. C. *Magnesium and Man,* 1980; Elin, R. J. Clin. Chem. 33:1965–1970, 1987; Wills, M. R. et al. Magnesium 5:317–327, 1986; Aikawa, J. K. *Magnesium:Its Biologic Significance,* CRC Press, Boca Ratan, 1981). While this procedure is capable of measuring free Mg$^{2+}$, it is fraught with a multiplicity of problems (need to control pH, need to control filter composition, time-consuming, inability to access whole blood Mg$^{2+}$, need for centifugation of blood). In addition, and most important, these classical methods, which primarily depend upon modifications of the procedure outlined by Watchorn, E. et al.( Biochem. J. 26:54, 1932), Toribara et al. (J. Clin. Invest. 36:738, 1957) and Walser, M. (J. Clin. Invest. 40:723–730, 1961) result in ionized Mg$^{2+}$ values on normal subjects which are significantly different from those obtained by the present method as assessed by ultrafiltration or using an ion selective electrode (ISE). Using ultracentrifigation methods combined with ultrafiltration methods to assess free Mg$^{2+}$, the percentages of ultrafilterable Mg reported by previous workers (around 70%) (Cummings, N. A. et al. Anal. Biochem 22:108–116, 1968; Nielson, S. P. Scand. J. Clin. Lab. Invest. 23:219–225, 1960) are much higher than the values using the present method. Even more recent measurements, using ultrafiltration and a micropartition filtration system has yielded a much wider range of values for ultrafilterable Mg from normal human subjects than those of the present method (D'Costa, M. et al. Clin. Chem. 29:519, 1983; Zaloga, G. P. et al. Crit. Care Med. 15:813–816, 1987). Some of these pitfalls preclude determination of Mg$^{2+}$ in various body fluids. Moreover, determinations can not be done on less than 1.0 ml of blood.

The physiologic or pathophysiologic effects of mild to severe (or graded) decreases or increases in extracellular free Mg$^{2+}$ in whole blood, serum or plasma has not been possible to discern in human subjects or animals either rapidly (e.g., within 1–2 min) or repeatedly (multiple samples over a few minutes-hours). Since Mg is frequently used in normomagnesemic patients for its antiarrhythmic, vasomotor and neuronal actions [Altura, B. M. et al. Drugs 28(Suppl.I): 120–142, 1984; Wacker, W. E. C. Magnesium and Man, 1980 Altura, B. M. et. al. In: *Metal Ions in Biological Systems,* 1990;Iseri C. T. et al. West J. Med. 138:823–828, 1983; Ebel, H. et al. J. Clin. Chem. Clin. Biochem. 21:249–265, 1983], it is vital to be able to assess the exact extracellular level of ionized Mg$^{2+}$ at any one instant. Although there is a dire need to carefully monitor extracellular Mg$^{2+}$ in hypomagnesemic patients or patients linked to Mg deficiency states such as cardiovascular insufficiency, cardiac arrhythmias, coronary artery spasm, those at risk for sudden death, renal disorders, respiratory muscle weakness, pre-eclampsia, eclampsia, migraine, hypertension, premenstrual syndrome, tetany, seizures, tremor, apathy, depression, hypokalemia and hypocalcemia, there is at present no way to do this either precisely or rapidly [Altura, B. M. et al. Drugs 28(Suppl.1):120–142, 1984; Wacker, W. E. C. *Magnesium and Man,* 1980; Altura, B. M. et. al. In: *Metal Ions in Biological Systems,* 1990; Iseri, C. T. West J. Med. 138:823–828, 1983; Ebel, H. et al. J. Clin. Chem. Clin. Biochem. 21:249–265, 1983;Altura, B. M. et al. Magnesium 4:226–244, 1985; Zaloga, G. P. Chest 56:257–258, 1989; Sjogren, A. J. Intern. Med. 226:213–222, 1989; Zaloga, G. P. et al. In: *Problems in Critical Care,* ed. G. P. Zaloga Vol 4:425–436, J.B. Lippincott Co., Philadelphia, 1990; Resnick, L. M. et al. Proc. Nat. Acad. Sci. U.S.A. 81:6511–6515, 1984; Rudnick, M. et al. APMIS 98:1123–1127, 1990].

In 1980, it was suggested on the basis of in-vitro experiments that drops in ionized serum Mg$^{2+}$ would produce coronary vasospasm, arrhythmias and sudden death (Turlapaty and Altura, Science 208:198–200, 1980) . Although clinical observations from other workers in the intervening years have suggested this might be a "real" possibility, up until the present invention, no evidence could be gathered due to the unavailability of a method for accurate and rapid assessment of blood ionized $Mg^{2+}$ (Altura, B. M. et al. In:*Metal Ions in Biological Systems*, Vol 26, 1990; Ebel, H. et al. J. Clin. Chem. Clin. Biochem. 21:249–265, 1983; Altura, B. M. et al. Magnesium 4:226–244, 1985; Sjogren, A. et al. J. Intern. Med. 226:213–222, 1989; Zaloga, G. P. et al. In: *Problems In Critical Care* Vol 4, 1990).

Over the past 10 years, it has been determined that reductions in ionized $Mg^{2+}$, experimentally in animals and isolated cerebral blood vessels, can induce intense vasospasm and rupture of blood vessels in the brain (Altura, B. M. et al. In: *Metal Ions in Biological Systems* Vol 26, 1990; Altura, B. T. et al. Neuroscience Letters 20:323–327, 1980; Altura, B. T. et al. Magnesium 1:277–291, 1982; Altura, B. T. et al. Magnesium 3:195–211, 1984; Altura, B. M. et al. Am. J. Emerg. Med. 1:180–193, 1983; Huang, Q–F., et al. FASEB J. 3:A845, 1989). On the basis of such experimental findings, it has been hypothesized that head trauma would be associated with deficits in serum, plasma and whole blood ionized $Mg^{2+}$ (Altura, B. T. et al. Magnesium 1:277–291, 1982; Altura, B. T. et al. Magnesium 3:195–211, 1984; Altura, B. M. et al. Am. J. Emerg. Med. 1:180–193, 1983). The present inventions has allowed these studies to be undertaken for the first time.

In the 1970's and 1980's, on the basis of numerous animal experiments, it was reported that deficits in ionized $Mg^{2+}$ would result in maintained peripheral vasospasm, constriction of small blood vessels in numerous organ regions and as a consequence development of high blood pressure or hypertension (Altura, B. M. et al. Drugs 28 (Suppl.I) :120–142, 1984; Altura, B. M. et al. In: *Metal Ions in Biological Systems* Vol 26, 1990; Altura, B. M. et al. Magnesium 4:226–244, 1985; Sjogren, A. et al. J. Intern. Med. 226:213–222, 1989;Turlapaty, P.D.M.V. et al. Science 208:198–200, 1980; Altura, B. M. et al. Federation Proc. 40:2672–2679, 1981; Altura, B. M. et al., Science 221:376–378, 1983; Altura, B. M. et al. Science 223:1315–1317, 1984). Until the development of the present invention, this hypothesis was not testable because of a lack of proper methodology for processing samples and measuring ionized $Mg^{2+}$.

In 1981–1983, studies on isolated blood vessels from animals and pregnant women, suggested that reduction in dietary intake of Mg or inability to metabolize Mg properly could result in reduction in ionized $Mg^{2+}$ and thus in umbilical and placental vasospasm, possibly reducing oxygen and nutrients to the growing fetus (Altura, B. M. et al. Federation Proc. 40:2672–2679, 1981; Altura, B. M. et al., Science 221:376–378, 1983). The end result could be, in large measure, responsible for fetal growth retardation, pre-eclampsia, hypertension and convulsions, particularly in pregnant indigent women (Rudnick, M. et al. APMIS 98:1123–1127, 1990; Altura, B. M. Science 221:376–378, 1983). Mg has been recommended as early as 1925 in this country for treatment and prevention of pregnancy-induced pre-eclampsia, hypertension and convulsions, but a method for accurately monitoring ionized $Mg^{2+}$ rapidly and repeatedly throughout pregnancy was not available until development of the present invention.

A novel method to draw, handle, process and store biological samples for accurate, rapid and reproducible levels of ionized or free $Mg^{2+}$ was developed. The method of collecting and processing samples has utility in preparing biological samples for measurement of ionized $Mg^{2+}$ concentrations using a novel selective ion electrode with neutral carrier based membrane or using the ultrafiltration procedure followed by atomic absorption. Using the methods of the present invention an accurate normal range for ionized $Mg^{2+}$ in whole blood, plasma and serum has been determined for the first time. It is now possible to diagnose, prognose and treat various disease states by the method of the present invention, by monitoring fluctuations in ionized $Mg^{2+}$ concentrations.

SUMMARY OF THE INVENTION

The present invention relates to a method for preparing biological samples, including collection and storage conditions, prior to testing for ionized $Mg^{2+}$ concentrations under conditions which minimize or prevent exchange of gases between the biological sample and atmospheric air and in which $O_2$ is substantially excluded from the biological sample, preferably under anaerobic conditions, prior to measuring ionized $Mg^{2+}$.

Another aspect of the invention is a method for determining ionized $Mg^{2+}$ concentrations in a biological sample, collected and maintained under anaerobic conditions or conditions which minimize or prevent exchange of gases between the biological sample and atmospheric air and in which $O_2$ is substantially excluded from the biological sample, the $Mg^{2+}$ concentration being measured using an ion selective electrode with a neutral carrier based membrane. In another embodiment, the $Mg^{2+}$ concentration is measured using atomic absorption on an ultrafiltrate.

Another aspect of the invention is a method for determining ionized $Ca^{2+}:Mg^{2+}$ ratios in a biological sample, collected and maintained under anaerobic condition or conditions which minimize or prevent exchange of gases between the biological sample and atmospheric air and in which $O_2$ is substantially excluded from the biological sample, the $Ca^{2+}$ and $Mg^{2+}$ concentrations being measured using ion selective electrodes with a neutral carrier based membrane. In another embodiment, the $Ca^{2+}$ and $Mg^{2+}$ concentrations are measured using atomic absorption spectroscopy on an ultrafiltrate.

An additional aspect of the invention is a method for diagnosing or prognosing disease states such as cardiac diseases, hypertension, lung diseases, abnormal pregnancy, pre-eclampsia eclampsia, head trauma, fetal growth retardation, and the like, in a patient using a method of determining ionized $Mg^{2+}$ concentrations or ionized $Ca^{2+}:Mg^{2+}$ ratios.

A further aspect of the invention is a method of maintaning normal ionized $Mg^{2+}$ concentrations in a patient in need of such maintenance comprising administration of $Mg^{2+}$.

BRIEF DESCRIPTION OF DRAWINGS

These and other objects, features, and many of the attendant advantages of the invention will be better understood upon a reading of the following detailed description whey considered in connection with the accompanying drawings wherein.

DETAILED DESCRIPTION OF THE INVENTION

The present invention relates to a method for preparing biological samples, including collection and storage conditions, prior to testing for ionized $Mg^{2+}$ concentrations which allow accurate and reproducible readings. More specifically, the invention relates to a method of collecting and maintaining biological samples under conditions which minimize or prevent exchange of gases between atmospheric air and the biological sample, preferably in which $O_2$ is substantially excluded and $pCO_2$ levels are maintained in the biological sample prior to measuring ionized $Mg^{2+}$. The preferred embodiment is a method for preparing and storing biological samples under anaerobic conditions.

The biological sample to be tested for ionized $Mg^{2+}$ is preferably a fluid or a sample that can be made fluid including but not limited to whole blood, plasma, serum, amniotic fluid, umbilical cord blood, cerebral spinal fluid, urine, gastric secretions, lacrimal secretions, peritoneal fluid, pleural fluid and the like obtained from animals, preferably mammals, most preferably humans. The fluid portion of biological tissue samples may be tested after homogenation with a tissue homogenizer or the like if collected and maintained under conditions described herein. In the preferred embodiment, the biological sample is whole blood, plasma, serum, cerebral spinal fluid, umbilical cord blood, and amniotic fluid.

Another aspect of the invention is a method for determining ionized $Mg^2$+concentrations in a biological sample, collected and maintained under conditions which minimize or prevent exchange of gases between the biological sample and atmospheric air, preferably in which $O_2$ is substantially excluded and $pCO_2$ levels are substantially maintained in the biological sample prior to measuring ionized $Mg^{2+}$, most preferably under anaerobic conditions. In one embodiment, the ionized $Mg^{2+}$ concentration is measured using an ion selective electrode with a neutral carrier based membrane. In another embodiment, the ionized $Mg^{2+}$ concentration is measured using atomic absorption spectroscopy on an ultrafiltrate. In a preferred embodiment, the ionized $Mg^{2+}$ concentration is obtained through the use of an ion selective electrode manufactured by Nova Biomedical, Waltham, Mass.

Another aspect of the invention is a method for determining ionized $Ca^{2+}:Mg^{2+}$ ratios in a biological sample, collected and maintained under conditions which minimize or prevent exchange of gases between the biological sample and atmospheric air, preferably in which $O_2$ is substantially excluded and $pCO_2$ levels are substantially maintained in the biological sample prior to measuring ionized $Ca^{2+}$ and $Mg^{2+}$, most preferably under anaerobic conditions. In one embodiment, the ionized $Ca^{2+}$ and $Mg^{2+}$ concentrations are measured using ion selective electrodes with a neutral carrier based membrane. In another embodiment, the ionized $Ca^{2+}$ and $Mg^{2+}$ concentration are measured using atomic absorption spectroscopy on an ultrafiltrate. In a preferred embodiment, the ionized $Ca^{2+}$ and $Mg^2$+concentrations are obtained through the use of an ion selective electrode manufactured by Nova Biomedical.

Ion selective electrodes based on neutral carrier membranes and the methods their use are known in the art and are widely used as integrated devices in clinical chemistry analyzers. With their availability, a selective determination of different ions in dilute samples as well as whole blood is possible (Oesch, U. et al. Clin. Chem 32(8):1448, 1988). Neutra carrier based membranes selective for specific ions are known in the art as described by Dinten, 0. et al. (Anal. Chem. 63:596–603, 1991), which is incorporated by reference. As examples, membranes composed of N,N'-diheptyl-N,N'-dimethyl-1,4-butanediamide ($C_{20}H_{40}N_2O_2$) (ETH 1117), N,N'-diheptyl-N,N'-dimethyl-aspartdiamide ($C_{20}N_{41}N_3O_2$) (ETH 2220), N,N"-octamethylenebis(N'-heptyl-N'-methyl-2-methylmalondiamide) ($C_{32}H_{62}N_4O_4$) (ETH 5214), N,N"-octamethylenebis(N',N'-dioctylmalondiamide) (ETH 5220), N',N",N"-iminodi-6,1-hexanediyldiiminotris(N-heptyl-N-methylmalonamide) ($C_{45}H_{84}NO_6$) (ETH 5282) and the like are known neutral carriers selective for $Mg^{2+}$. Some examples of neutral carriers selective for $Ca^{2+}$ are (–)-(R,R)-N,N'-[bis(11-ethoxycarbonyl)undecyl]-N,N', 4,5tetramethyl-3,6-dioxaoctanediamide ($C_{38}H_{72}N_2O_8$) (ETH 1001),N,N,N',N'-tetracyclohexyl-3-oxapentanediamide ($C_{28}H_{48}N_2O_8$) (ETH 129), N,N-dicyclohexyl-N',N'-dioctadecyl-3-oxapentanediamide (ETH 5234) and the like.

The methods for determining the ionized $Ca^{2+}$ and $Mg^{2+}$ concentration are measured using atomic absorption spectroscopy on an ultrafiltrate are known in the art as described by, Walser, M. (J. Clin. Invest. 40:723–730, 1961), D'Costa, M. (Clin. Chem. 29:519, 1983), and Zaloga, G. P. et al. Crit. Care Med. 15:813–816, 1987), which are incorporated by reference.

Another aspect of the invention is a method for diagnosing or prognosing disease states or conditions associated with Mg deficiencies using a method of determining ionized $Mg^{2+}$ or ionized $Ca^{2+}:Mg^{2+}$ ratios in a biological sample, collected and maintained under conditions which minimize or prevent exchange of gases between the biological sample and atmospheric air, preferably in which $O_2$ is substantially excluded and $pCO_2$ levels are substantially maintained in the biological sample prior to measuring ionized $Ca^{2+}$ and $Mg^{2+}$, most preferably under anaerobic conditions. Such disease states include cardiac diseases, cardiovascular insufficiency, cardiac arrhythmias, coronary artery spasm, those at risk for sudden death, renal disorders, lung diseases, respiratory muscle weakness, abnormal pregnancy, preeclampsia, eclampsia, fetal growth retardation, migraine, hypertension, head trauma, premenstrual syndrome, tetany, seizures, tremor, apathy, depression, hypokalemia and hypocalcemia. The $Mg^{2+}$ values of the patient are compared to normal ionized $Mg^{2+}$ values for biological samples. In one embodiment, the normal ionized $Mg^{2+}$ concentration approximately 0.53 to 0.66 mM for the biological sample of whole blood, serum, and plasma.

A further aspect of the invention is a method of maintaining normal ionized $Mg^{2+}$ concentrations in a patient in need of such maintenance by administering ionize d $Mg^{2+}$ in a concentration sufficient to maintain levels of ionized $Mg^{2+}$ in biological samples within a normal range of ionized $Mg^{2+}$.

EXAMPLE I

Sample Collection

Figure 1:
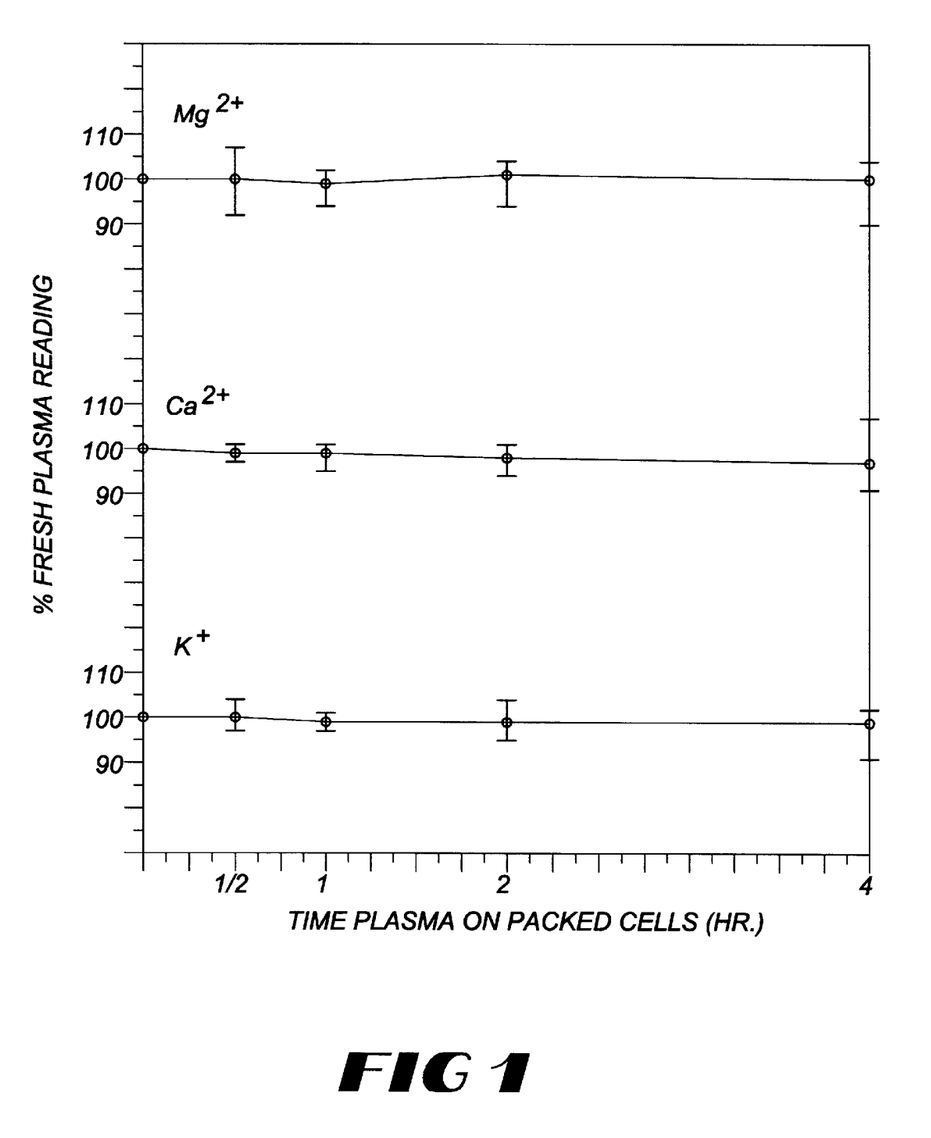
FIG. 1 shows the plasma ionized $Mg^{2+}$ concentrations from the whole blood which was spun to pack the formed elements such as erythrocytes, and stored anaerobically for 4 hours at room temperature. It shows that whole blood can be stored for at least 4 hours if stored anaerobically without affecting the ionized $Mg^{2+}$ values as compared to an ionized $Mg^{2+}$ concentration for fresh plasma.

In order to obtain precise and reproducible determinations of ionized $Mg^{2+}$ with the ISE, blood samples were collected under conditions that minimize or prevent exchange of atmospheric gases with those of the sample, most preferably under anaerobic conditions into a tube with the air evacuated, such as a Vacutainer™ tube, or other tube or syringe substantially free of atmospheric gases, especially $O_2$. The tube or syringe may contain heparin (<75 u/ml). After collection of the biological sample, the samples are placed in and kept under conditions that minimize or prevent exchange of atmospheric gases with those of the sample, most preferably under anaerobic conditions (FIG. 1).

EXAMPLE II

Sample Processing

To process clotted blood or plasma (heparinized blood), the samples were maintained under conditions that minimize or prevent exchange of gases between atmospheric air and the biological sample, preferably anaerobic conditions in tubes sealed with rubber stoppers. Parafilm or plastic and glass tops cannot be utilized as this allows for air to enter the sample. If samples (i.e., whole blood, serum or plasma) were analyzed (or frozen) more than 30 min after blood draw for processing of serum or plasma, the sealed tubes were place in a standard clinical or laboratory centrifuge and centrifuged at 3,000–4,000 rpm for 15–20 minutes. After this time, the sera or plasma was carefully removed from the packed cells by inserting a sterilized needle attached to either a plastic syringe (for sera) or a lightly heparinized (<75 u/ml) glass syringe (for plasma) or a similar device.

EXAMPLE III

Sample Storage

Figure 2:
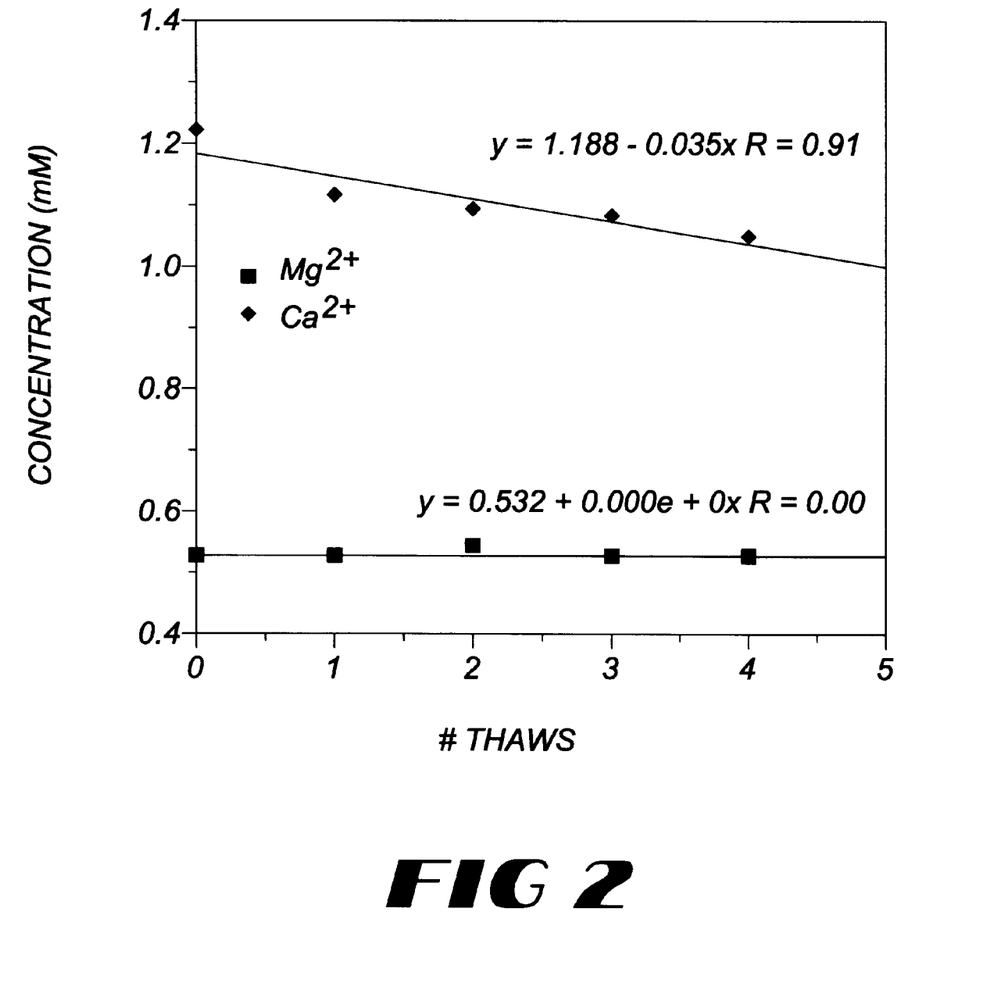
FIG. 2 shows that freeze-thawing samples has virtually no effect on the ionized $Mg^{2+}$ values for samples stored under anaerobic conditions. In contrast, ionized $Ca^{2+}$ values decline with repeated freeze-thawing of the sample.

The anaerobically maintained samples were either processed with the ISE within six hours or the plasma or serum carefully expelled into a tube with the air evacuated or other tube or syringe substantially free of atmospheric air, especially $O_2$, most preferably anaerobic, with or without heparin, and frozen at $-10°$ C. Unlike ionized $Ca^{2+}$, ionized $Mg^{2+}$ levels were stable during numerous subsequent freeze-thaw procedures, provided the bloods were drawn and processed under anaerobic conditions as described above (see FIG. 2, Table 1). Under conditions where parafilm coverings were used, pH and $pCO_2$ changes occurred causing erratic and erroneous ionized $Mg^{2+}$ values.

TABLE 1

Influence of Freeze-Thawing with Parafilm covering on Plasma pH and Ionized Free $Mg^{2+}$ Obtained with an Ion Selective Electrode

| Parameter | Day of Examination | | | |
|---|---|---|---|---|
| | 1 | 2 | 3 | 12 |
| pH | 7.435 | 7.685 | 7.897 | 8.26 |
| | ± | ± | ± | ± |
| | 0.010 | 0.044 | 0.056 | 0.070 |
| $Mg^{2+}$ (mM) | 0.64 | 0.65 | 0.60 | 0.53 |
| | ± | ± | ± | ± |
| | 0.035 | 0.04 | 0.029 | 0.036 |

Using the method of the present invention, plasma and serum samples were frozen for up to two weeks at $-10°$ C. without affecting the ionized $Mg^{2+}$ values. Whole blood samples were maintained under anaerobic conditions at room temperature for up to six hours after blood draws prior to ionized $Mg^{2+}$ determinations. These and other experiments clearly indicated that as the biological samples such as blood, sera or plasma became exposed to air, they loose $CO_2$, and as a consequence the pH became alkaline. This adversely affected the ionized free $Mg^{2+}$ values resulting in erroneous readings. This is completely obviated with proper handling as describe for this invention.

EXAMPLE IV

Figure 3:
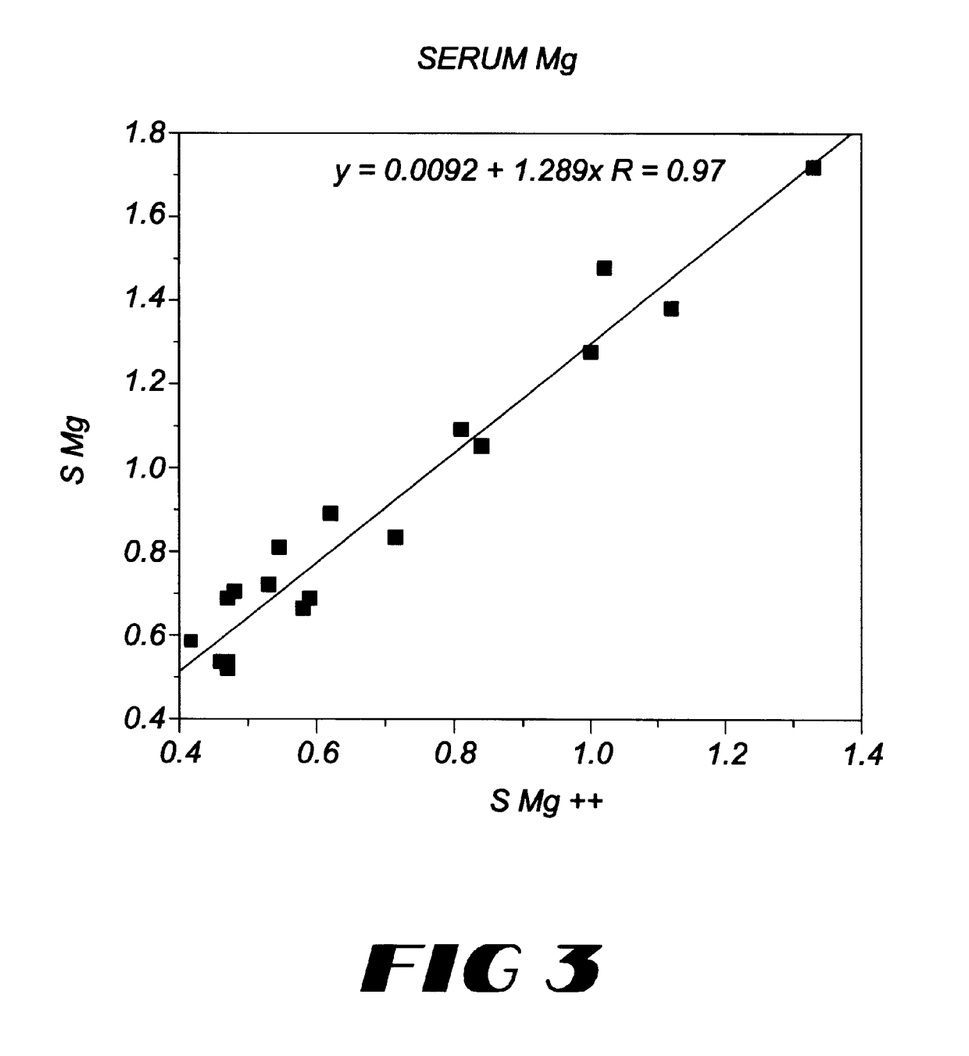
FIG. 3 shows the correlation between serum $Mg^{2+}$ values as measured on ultrafiltrate $Mg^{2+}$ by atomic absoprtion vs. ionized $Mg^{2+}$ values determined by an ISE. There was a correlation of R=0.97 which indicates that the two methods are comparable the samples are processed anaerobically.

Comparison Of Ionized $Mg^{2+}$ Values Using A Ion Selective Neutral Carrier Membrane Electrode vs. Ultrafiltration A comparison of human serum or plasma ionized $Mg^{2+}$ obtained on fresh samples as measured by a ion selective neutral carrier membrane electrode versus serum Mg obtained on ultrafiltration (=ionized $Mg^{2+}$) using atomic absorption spectrophotometry showed an excellent correspondence between values (see FIG. 3) when samples were processed anaerobically. Studies were conducted to determine if ionized $Mg^{2+}$ values determined by ISE were comparable to values measured on ultrafiltrate $Mg^{2+}$ ($uMg^{2+}$) by atomic absorption. Whole blood, plasma, and serum were taken from healthy normal humans and processed anaerobically as described above. The results showed that the ionized $Mg^{2+}$ values obtained for whole blood, plasma, serum by ISE and values for ultrafiltrates were virtually the same [e.g., in millimolar concentrations (mM), 0.60±0.005 in whole blood, 0.59±0.008 for plasma; 0.59±0.006 for serum; 0.58±0.010 for $uMg^{2+}$]. Assessment of ionized $Mg^{2+}$ in whole blood, plasma and serum with the ISE indicate that ionized $Mg^{2+}$ is held within an extremely narrow range (0.53–0.66 mM) when compared to total Mg (0.75–1.05 mM) or ionized $Ca^{2+}$ (1.09–1.30 mM). This narrow range for ionized $Mg^{2+}$ has not previously been reported. These data were derived from approximately 60 normal healthy human subjects. Such a narrow range for ionized $Mg^{2+}$ obtained with the ISE suggested that slight changes in the normal ionized $Mg^{2+}$ range could be diagnostic and prognostic for numerous pathophysiologic states and disease conditions in animals and humans subjects (Altura et al. Clinical Res., in press; Handwerker, S. et al. Magnesium and Trace Elements, in press; Altura et al. Magnesium and Trace Elements, in press).

EXAMPLE V

Precision and Reproducibility

Using the ISE on three levels of aqueous $Mg^{2+}$ controls, mean values over a range of 0.3 to 1.0 mM are within 94.6 and 99.2% of their targets. The linearity of the ISE (0.1–3.0 mM) in aqueous solution and human plasma and serum ranges between 92.0 and 99.3%.

EXAMPLE VI

Specificity And Possible Interferents

The ISE is highly selective for ionized magnesium ($IMg^{2+}$), exhibiting no or negligible effects from physiologic concentrations of $Ca^{2+}$, $Na^+$, $K^+$, or $H^+$. Ligand binding studies indicate that pathophysiologic concentrations of $SO_4^{2-}$, heparin, lactate, acetate, $PO_4^{2+}$ or $HCO_3^{31}$ anions fail to interfere with measurement in aqueous solution, plasma, or serum. Likewise, pathophysiological concentrations of $Fe^{3+}$, $Cu^{2+}$, $Zn^{2+}$, $CA^{2+}$, or $Pb^{2+}$ do not interfere with ISE measurements of $Mg^{2+}$. Since atomic absoprtion spectroscopy when conducted in the presence of adequate amounts of lanthanum is specific for total Mg, none of these ligands interfere with Mg determinations.

EXAMPLE VII

Diagnosis & Prognosis In Cardiovascular Disease

It has been suggested that abnormalities in Mg metabolism may play an important role in the etiology of cardiac diseases (Altura, B. M. Drugs 28 (Suppl.I): 120–142, 1984; Altura, B. M. et al. In: *Metal Ions in Biological Systems* Vol 26, 1990; Iseri, C. T. West. J. Med. 138:823–828, 1983; Ebel, H. et al. J. Clin. Chem. Clin. Biochem. 21:249–265, 1983; Altura, B. M. et al. Magnesium 4:226–244, 1985; Sjogren, A. et al. J. Intern Med. 226:213–222, 1989; Zaloga, G. P. et al. In:Problems in Critical Care Vol 4, 1990; Rudnick, M. et al. APMIS 98:1123–1127, 1990). Although elevated extracellular $Mg^{2+}$ is widely used in connection with cardiopulmonary bypass (CPB) procedures, it is not known whether such procedures result in rapid and sequential alterations in blood ionized $Mg^{2+}$ levels. By using the methods of the present invention, ionized $Mg^{2+}$, along with ionized $Ca^{2+}$ levels in plasma were monitored in patients prior to, during, and after CPB. The patients studies ranged in age from 10–80 yrs. and were scheduled for coronary bypass, valve replacement or other elective open-heart procedures (OHP). On the basis of studies with 30 human subjects prior to and during cardiopulmonary bypass (CPB), subjects had lower than normal ionized $Mg^{2+}$ prior to surgery (Altura, B. T. et al. Clin. Chem July–August, 1991; Altura, B. T. et al. Clin. Res., in press; Altura, B. T. et al. Magnesium and Trace Elements, in press). Assessment of ionized $Mg^{2+}$ in plasma revealed the following [means±S.E.M. in millimolar conc (mM)]: prior to OHP= 0.56 ±0.03 vs 0.60±0.005 (control); within 10–15 minutes of CPB=0.89±0.08; post perfusion=0.75±0.03. In addition, on the basis of frequent determinations during CPB, using an ion selective electrod the degree of spontaneous hypotension, arrhythmias, and coronary vasospasm during and post-surgery were correlated to the pronounced alterations in ionized $Ca^{2+}$:ionized $Mg^{2+}$ ratios. (Altura, B. T. et al. Clin. Res., in press; Altura, B. T. et al. Magnesium and Trace Elements, in press). With respect to ionized $Ca^{2+}$, the respective values were 0.96±0.016 vs. 1.21±0.01; 0.79±0.02; and 1.23±0.10. Although the normal ionized $Ca^{2+}$:ionized $Mg^{2+}$ ratio is 1.95–2.18, all patients studied prior to CPB exhibited lower values (mean=1.72±0.09). Within 10–15 minutes of initial CPB, the ionized $Ca^{2+}$:ionized $Mg^{2+}$ ratio fell almost 50% (mean=0.91±0.10); post-perfusion, the ratio rose to 1.62±0.18. Overall, these data indicate that ionized $Mg^{2+}$ concentrations can be monitored in plasma during CPB. Predictable patterns arose out of these studies, showing that cardiac disease patients tend to exhibit lower than normal ionized $Mg^{2+}$, ionized $Ca^{2+}$ and ionized $Ca^{2+}$:ionized $Mg^{2+}$ ratios. Additionally, the hypotension observed upon initiation of CPB may in part be a reflection of elevated ionized $Mg^{2+}$ and a pronounced drop in the ionized $Ca^{2+}$:ionized $Mg^{2+}$ ratio. Such patterns are therefore diagnostic and predictive, thus allowing the physician and surgeon to carefully monitor and treat such cardiac patients.

EXAMPLE VIII

Diagnosis and Prognosis in Head Trauma

The present studies were undertaken to determine if head trauma was associated with deficits in serum, plasma and whole blood ionized $Mg^{2+}$ and to determine if the degree of head injury would correlate with the degree of the plasma ionized $Mg^2+$ deficiency. Studies of more than 30 head trauma patients clearly demonstrated that head trauma and the degree of head trauma was associated with deficiencies in ionized $Mg^{2+}$. The range of ionized $Mg^{2+}$ in plasma of these head trauma cases was significantly below normal (i.e., 0.33–0.53) with a mean plasma ionized $Mg^{2+}$= 0.46±0.026 or almost 40% lower than normal; the greater the degree of head trauma (as assessed by clinical signs and Glasgow scores), the greater the deficit in ionized $Mg^{2+}$. Therefore, the pattern is diagnostic and prognostic. Deficiencies in ionized $Mg^{2+}$ may indicate that specific regions of brain are affected by the trauma. The present invention allows the physician to monitor ionized $Mg^{2+}$ and ionized $Ca^{2+}$:ionized $Mg^{2+}$ ratios for diagnosis and prognostic purposes.

EXAMPLE IX

Diagnosis & Prognosis in Hypertension

Applicants hypothesized that many hypertensive human subjects might be expected to exhibit reduction in ionized $Mg^{2+}$ (Altura, B. M. et al. Federation Proc. 40:2672–2679, 1981; Altura, B. M. et al. Science 223:1315–1317, 1984) and that treatment of such hypertensive subjects would restore ionized $Mg^{2+}$ to normal. Therapy of such patient. should be signified by adjustments of plasma ionized $Mg^{2+}$ and would be a valuable adjunct for diagnosis and treatment of such patients. Data on more than 30 normotensive (0.52–0.66 mM), untreated hypertensive (0.42–0.60) and treated hypertensives (0.56–0.63), using the methodology of the present invention, supported this idea. Monitoring ionized $Mg^{2+}$ concentrations in humans or animals, by the present invention, now makes it possible to diagnose, prognose and treat hypertensive subjects.

EXAMPLE X

Diagnosis & Prognosis in Pregnancy-Induced Pre-Eclampsia, Hypertension, Convulsions and Fetal Growth Retardation Using the present method of sample processing and an ISE for measuring ionized $Mg^{2+}$, a study was undertaken to determine ionized and total Mg levels in umbilical venous and arterial blood in normal and abnormal pregnant patients. Correlations were made between $Mg^{2+}$ levels and maternal and neonatal pathological states. The study consisted of 30 pregnant patients of which 17 had no maternal or neonatal complications and 13 had one or more of the following abnormalities: toxemia, transient hypertension, gestational diabetes premature labor during the current pregnancy or delivery prior to 38 weeks, growth retarded newborn, chorioamnionitis, or ABO incompatibility in the newborn. All APGAR scores were 9,10. There were no differences between the groups with regard to maternal age, race parity, percentage of indigent patients, mode of delivery, epidural analgesis, use of Pitocin, use of oxygen in labor, ECA at delivery, mean birth weight or sex of newborn. Three patients in the abnormal group received Mg therapy for toxemia and had venous samples taken. The results are expressed as mean (mM)±SEM. In normal pregnancies, the mean umbilical venous plasma (or serum) ionized $Mg^{2+}$ level was 0.52±0.014 (N=16), which approximates the lower end of the normal range values in the venous plasma of non-pregnant women. The mean umbilical arterial ionized $Mg^{2+}$ level in normal pregnancies was 0.51±0.020 (N=5), demonstrating no significant differences in the amount of ionized $Mg^{2+}$ which enters or leaves the fetus.

Pregnant women who had one or more of the various maternal pathological conditions listed above had a significantly lower mean venous plasma or serum ionized $Mg^{2+}$ level (0.44±0.014) than the normal group. The subgroup of pregnant women who exhibited transient hypertension had a mean venous ionized $Mg^{2+}$ level of 0.43±0.015, which is almost a 20% deficit compared to the normal group. Two patients that had chorioamnionitis had the lowest values of umbilical venous $Mg^{2+}$ in the entire study population, 0.25 mM and 0.38 mM. The per cent of the total Mg which was ionized was 67.3±1.89 in the normal pregnancies and 64.5±2.31 in the abnormal ones, an insignificant difference. One of the patients with chorioamnionitis had only 49% ionized $Mg^{2+}$, however.

These data indicate that serum or plasma ionized $Mg^{2+}$ levels in pregnancy are of diagnostic value. Transient hypertension in labor is associated with hypomagnesemia, which could account in large measure for the increase in blood pressure. Therefore, the present methodology for use in monitoring ionized $Mg^{2+}$ concentrations throughout pregnancy allows the obstetrician to prevent pregnancy-induced pre-eclampsia, hypertension, convulsions and fetal growth retardation by treatment of the women with ionized $Mg^{2+}$ when levels drop abnormally low. Furthermore, ionized $Mg^{2+}$ levels may be a biochemical marker for following disease processes in pregnant women and their response to treatment.

EXAMPLE XI

Ionized $Ca^{2+}:Mg^{2+}$ Ratios

Since determinations of ionized $Ca^{2+}$ have been suggested to be of value in critical care medicine (Zaloga, G. P. et al. Crit. Care Med. 15:813–816, 1987; Olinger, M. L. The Emerg. Med. Clin. N. Amer. 7:795–822, 1989) and significant alterations in ionized $Mg^{2+}$ can be measured using the present methods, it is reasonable to examine and utilize $Ca^{2+}:Mg^{2+}$ ratios in the diagnosis and treatment of disease states where both of these cations could be expected to exhibit subtle changes in body fluids. The data described herein, particularly for cardiac patients and such patients on cardiopulmonary bypass indicate that the $Ca^{2+}:Mg^{2+}$ ratios are significantly diagnostic and prognostic markers for hypotension, coronary vasospasm and dysrhythmias during and post cardiac surgery. Additionally, $Ca^{2+}:Mg^{2+}$ ratios may be diagnostic and prognostic in determining the severity and progression of head trauma, abnormal pregnancies, and hypotension.

EXAMPLE XII

Treatment of Hypo- and Hyper-Magnesemia States

Use of the present invention allows the physician, veterinarian and researcher to scientifically monitor and treat hypo- or hypermagnesemia states.

Candidates for treatment with $Mg^{2+}$ include animals, particularly mammals such as humans with coronary heart disease, congestive heart failure, hypomagnesemia, critical illnesses, lung diseases, abnormal pregnancy, undergoing cardiopulmonary bypass, head trauma, aminoglycoside (or other antibiotics) toxicity, chemotherapeutic drug-induced hypomagnesemia or those in high risk categories for heart attack or stroke such as those with hypertension, diabetes, high cholesterol, or smokers. The amount of $Mg^{2+}$ administered will, of course depend upon the severity of the condition being treated, the route of administration chosen, and the dose of $Mg^{2+}$, and ultimately will be decided by the attending physician or veterinarian. As a guide, a concentration of $Mg^{2+}$, as used in the prior art include regimens similar to those reported by clinicians for different disease states (Wacker, W. E. C. *Magnesium and Man,* 1980; Iseri, C. T. et al. West J. Med. 138:823–828, 1983; Zaloga, G. P. In: *Problems in Critical Care* Vol 4, 1990; Rudnick, M. et al. APMIS 98:1123–1127, 1990; Rasmussen, H. S. et al. Lancet 1:234–236, 1986; Berkelhammer, C. et. al. Canadian Med. Assoc. J. 312:360–368, 1985; Cohen, L. et al. Magnesium 3:159–163, 1984; Dyckner, T. et al. Brit. Med. J. 286:1847–1849, 1983; Olinger, M. L. The Emerg. Med. Clin. N. Amer. 7:795–822, 1989; Kobrin, S.M. et al. Sem. in Nephrol. 10:525–535, 1990). Use of the present methodology and assessment of ionized $Mg^{2+}$, rapidly, will make it possible to monitor a patient's response to therapeutic regimens in a precise and carefully controlled manner, which was heretofore not possible.

$Mg^{2+}$ may be administered by any route appropriate to the condition being treated including intravenous (IV), intraperitoneal, intramuscular, subcutaneous, oral, nasal, and the like. Preferably, the $Mg^{2+}$ is injected IV into the blood stream of the mammal being treated especially in acute cases of hypomagnesemia. It will be readily appreciated by those skilled in the art that the preferred route will vary with the condition being treated.

While it is possible for the $Mg^{2+}$ to be administered as the pure or substantially pure mineral, it is preferable to present it as a pharmaceutical formulation or preparation. Suitable bioavailable magnesium salts and magnesium compounds are well known in the art (U.S. Pat. No. 4,954,349 and U.S. Pat. No. 4,546,195).

The formulations for the present invention, both veterinary and for human use, comprise $Mg^{2+}$ together with one or more pharmaceutically acceptable carriers and optionally other therapeutic ingredients. The carrier(s) must be "acceptable" in the sense of being compatible with the other ingredients of the formulation and not deleterious to the recipient thereof. The formulations may conveniently be presented in unit dosage form and may be prepared by any method well known in the pharmaceutical art.

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A method for determining ionized $Mg^{2+}$ concentrations in biological samples comprising:
    (A) collecting the biological sample under conditions which substantially prevent exchange of gases between the biological sample and atmospheric air,
    (B) maintaining the biological sample under conditions which substantially prevent exchange of gases between the biological sample and atmospheric air prior to measurement of ionized $Mg^{2+}$, and
    (C) measuring ionized $Mg^{2+}$ concentrations of said biological samples using a selective ion electrode with a neutral carrier based membrane.

2. A method determining ionized $Mg^{2+}$ concentrations in biological samples comprising:
    (A) collecting the biological sample under conditions in which $O_2$ is substantially excluded,
    (B) maintaining the biological sample under conditions in which $O_2$ is substantially excluded prior to measurement of ionized $Mg^{2+}$, and
    (C) measuring ionized $Mg^{2+}$ concentrations of said biological samples using a selective ion electrode with a neutral carrier based membrane.

3. A method for determining ionized $Mg^{2+}$ concentrations in biological samples comprising:
- (A) collecting the biological sample under anaerobic conditions,
- (B) maintaining the biological sample under anaerobic conditions prior to measurement of ionized $Mg^{2+}$, and
- (C) measuring ionized $Mg^{2+}$ concentrations of said anaerobic biological sample using a selective ion electrode with a neutral carrier based membrane.

4. A method for determining ionized $Ca^{2+}:Mg^{2+}$ ratios based on an ionized $Ca^{2+}$ concentration: to an ionized $Mg^{2+}$ concentration in biological samples comprising:
- (A) collecting the biological sample under conditions which substantially prevent exchange of gases between the biological sample and atmospheric air,
- (B) maintaining the biological sample under conditions which substantially prevent exchange of gases between the biological sample and the atmospheric air prior to measurement of ionized $Ca^{2+}$ or $Mg^{2+}$, and
- (C) measuring ionized $Mg^{2+}$ concentrations of said biological sample using a selective ion electrode with a neutral carrier based membrane,
- (D) measuring ionized $Ca^{2+}$ concentrations of said biological sample and,
- (E) calculating the ionized $Ca^{2+}:Mg^{2+}$ ratio.

5. A method of claims 1–4, wherein the biological sample is whole blood, plasma, or serum.

6. A method of diagnosing an ionized magnesium imbalance in a patient comprising:
- (A) collecting the biological sample from the patient under conditions which substantially prevent exchange of gases between the biological sample and atmospheric air,
- (B) maintaining the biological sample under conditions which substantially prevent exchange of gases between the biological sample and atmospheric air
- (C) measuring ionized $Mg^{2+}$ concentration of said biological sample using a selective ion electrode with a neutral carrier based membrane, and
- (D) comparing the ionized $Mg^{2+}$ concentration of the patient to a normal ionized $Mg^{2+}$ concentration in order to diagnose the magnesium imbalance.

7. A method for diagnosing an ionized magnesium imbalance in a patient comprising:
- (A) collecting the biological sample from the patient under conditions in which $O_2$ substantially excluded,
- (B) maintaining the biological sample under conditions in which $O_2$ is substantially excluded prior to measurement of ionized $Mg^{2+}$,
- (C) measuring ionized $Mg^{2+}$ concentrations of said biological sample using a selective ion electrode with a neutral carrier based membrane,
- (D) comparing the ionized $Mg^{2+}$ concentration of the patient to a normal ionized $Mg^{2+}$ concentration in order to diagnose the magnesium imbalance.

8.) A method of diagnosing an ionized $Ca^{2+}:Mg^{2+}$ ratio imbalance in a patient comprising:
- (A) collecting a biological sample from the patient under conditions which substantially prevent exchange of gases between the biological sample and atmospheric air,
- (B) maintaining the biological sample under conditions which substantially prevent exchange of gases between the biological sample and atmospheric air prior to measurement of ionized $Ca^{2+}:Mg^{2+}$,
- (C) measuring ionized $Mg^{2+}$ concentrations in said biological sample using a selective ion electrode with a neutral carrier based membrane,
- (D) measuring ionized $Ca^{2+}$ concentrations in said biological sample, and (E) comparing the ionized $Ca^{2+}:Mg^{2+}$ ratio of the patient to a normal ionized $Ca^{2+}:Mg^{2+}$ ratio in order to diagnose the imbalance.

9. A method of maintaining normal ionized magnesium concentration in a patient in need of said maintenance comprising: administration of $Mg^{2+}$ in a concentration sufficient to maintain a level of ionized $Mg^{2+}$ concentration in a biological sample within a normal range of ionized $Mg^{2+}$ concentration, said concentration determined according to the method of claims 1–3.

10. A method of claim 6–8 wherein the normal ionized magnesium ion concentration is approximately 0.53 to 0.66 mM for the biological sample of whole blood, serum or plasma.

11. A method of claim 9 wherein the normal ionized magnesium ion concentration is approximately 0.53 to 0.66 mM for the biological sample of whole blood, serum or plasma.

12. In a method for diagnosing or prognosis of disease in a patient, the improvement comprising:
- (A) collecting a biological sample from the patient under conditions which substantially prevent exchange of gases between the biological sample and atmospheric air;
- (B) maintaining the biological sample under conditions which substantially prevent exchange of gases between the biological sample and atmospheric air;
- (C) measuring an ionized $Mg^{2+}$ concentration of said biological sample using a selective ion electrode with a neutral carrier based membrane; and
- (D) comparing the ionized $Mg^{2+}$ concentration of the patient to a normal ionized $Mg^{2+}$ concentration in order to diagnose or prognoses the disease.

13. In a method for diagnosis or prognosis of disease in a patient, the improvement comprising:
- (A) collecting a biological sample from the patient under conditions which substantially prevent exchange of gases between the biological sample and atmospheric air;
- (B) maintaining the biological sample under conditions which substantially prevent exchange of gases between the biological sample and atmospheric air;
- (C) measuring ionized $Mg^{2+}$ concentrations of said biological sample using a selective ion electrode with a neutral carrier based membrane;
- (D) measuring ionized $Ca^{2+}$ concentrations of said biological sample; and
- (E) comparing the ionized $Ca^{2+}:Mg^{2+}$ ratio of the patient to a normal ionized $Ca^{2+}:Mg^{2+}$ ratio in order to diagnose or prognose the disease.

14. A method of claim 12 or 13 wherein the disease comprises cardiac diseases, hypertension, lung disease, abnormal pregnancy, head trauma, migraine, renal diseases, or fetal growth retardation.

15. The method of claim 12 or 13, wherein the biological sample is whole blood, plasma or serum.

16. The method of claims 12 or 13, wherein the conditions are anaerobic.

17. The method of claims 12 or 13, wherein the normal ionized magnesium ion concentration is approximately 0.53 to 0.66 mM for the biological sample of whole blood, serum or plasma.

18. The method of claims 1–4, wherein the biological samples is cerebral spinal fluid, umbilical cord blood or amniotic fluid.

19. The method according to claim 6, 7 or 8, wherein the biological sample is whole blood, plasma or serum.

20. The method according to claim 6, 7 or 8, wherein the biological sample is cerebral spinal fluid, umbilical cord blood or amniotic fluid.

21. The method of claim 10, wherein the conditions are anaerobic.

22. The method of claim 6, 7 or 8, wherein the conditions are anaerobic.

* * * * *